United States Patent [19]

Matzinger et al.

[11] Patent Number: 5,780,304
[45] Date of Patent: Jul. 14, 1998

[54] METHOD AND APPARATUS FOR ANALYTE DETECTION HAVING ON-STRIP STANDARD

[75] Inventors: David Parkes Matzinger, Menlo Park; George Michael Daffern, Sunnyvale, both of Calif.

[73] Assignee: Lifescan, Inc., Milpitas, Calif.

[21] Appl. No.: 613,404

[22] Filed: Mar. 11, 1996

Related U.S. Application Data

[63] Continuation of Ser. No. 302,160, Sep. 8, 1994, abandoned.

[51] Int. Cl.[6] .................................................. G01N 21/75
[52] U.S. Cl. .................. 436/169; 422/68.1; 422/82.05
[58] Field of Search ............................. 422/68.1, 82.05, 422/56, 58; 436/169

[56] References Cited

U.S. PATENT DOCUMENTS

| | | | |
|---|---|---|---|
| 3,552,928 | 1/1971 | Fetter | 23/253 |
| 3,907,503 | 9/1975 | Betts et al. | 422/67 |
| 3,980,437 | 9/1976 | Kishimoto et al. | 23/253 TP |
| 3,992,158 | 11/1976 | Przybylowicz et al. | 23/253 TP |
| 4,042,335 | 8/1977 | Clement | 23/253 TP |
| 4,125,372 | 11/1978 | Kawai et al. | |
| 4,144,306 | 3/1979 | Figueras | 422/56 |
| 4,255,384 | 3/1981 | Kitajima et al. | 422/57 |
| 4,258,001 | 3/1981 | Pierce et al. | 422/56 |
| 4,292,272 | 9/1981 | Kitajima et al. | 422/57 |
| 4,452,887 | 6/1984 | Kitajima et al. | 435/14 |
| 4,509,859 | 4/1985 | Markart et al. | |
| 4,592,893 | 6/1986 | Poppe et al. | |
| 4,682,895 | 7/1987 | Costello | |
| 4,714,874 | 12/1987 | Morris et al. | 324/65 |
| 4,774,192 | 9/1988 | Terminiello et al. | 436/530 |
| 4,790,979 | 12/1988 | Terminiello et al. | 422/56 |
| 4,816,224 | 3/1989 | Vogel et al. | 422/55 |
| 4,978,503 | 12/1990 | Shanks et al. | |
| 4,994,238 | 2/1991 | Daffern et al. | 422/56 |
| 5,029,583 | 7/1991 | Meserol et al. | |
| 5,037,614 | 8/1991 | Makita et al. | |
| 5,059,394 | 10/1991 | Phillips et al. | |
| 5,082,516 | 1/1992 | Akao et al. | |
| 5,095,025 | 3/1992 | Tanaka et al. | |
| 5,095,026 | 3/1992 | Schoenwald et al. | |
| 5,120,507 | 6/1992 | Sano et al. | |

(List continued on next page.)

FOREIGN PATENT DOCUMENTS

| | | | |
|---|---|---|---|
| 0 456 098 A2 | 11/1991 | European Pat. Off. | G01N 33/52 |
| 0 574 134 A2 | 12/1993 | European Pat. Off. | G01N 33/52 |
| 40 35 052 A1 | 11/1989 | Germany | |
| 938029 | 8/1961 | United Kingdom | |
| 1037155 | 7/1966 | United Kingdom | |
| 2 090 659 | 7/1982 | United Kingdom | G01N 33/48 |
| WO94/18559 | 8/1994 | WIPO | G01N 33/52 |

OTHER PUBLICATIONS

Azo Dyes by Oxidative Coupling, VIII*, S. Hunig and Kobrich, Liebigs Ann. Chem. 617, 216 (1958).
Mechanism for Preventing Bending of Specimen for Urine; Japanese Patent Appl. 2-233741, Sep. 4, 1990.
New Contributions to the Optics of Intensely Light–Scattering Materials, Part I; Journal of Optical Society of America, vol. 38, No. 5, May 1948, pp. 448–457.

*Primary Examiner*—Lyle A. Alexander

[57] ABSTRACT

A test strip is provided for having liquid applied thereto and for determining the presence or quantity of an analyte in such liquid. Specifically, the test strip comprises a reaction zone which varies in reflectance as a function of the quantity of analtye present in the applied liquid. The strip is to be inserted into an optical reading apparatus. A standard zone is positioned on the strip so as to lead the reaction zone as the strip is inserted into the reading apparatus. The apparatus may then be provided with optical means for sequentially determining the reflectance value of the standard zone as the strip is being inserted into its fully inserted position in the apparatus and the reflectance value of the reaction zone after the strip has been inserted. The apparatus is further provided with means for calculating the presence and/or quantity of analyte in question as a function of the standard zone reflectance and the reaction zone reflectance.

3 Claims, 7 Drawing Sheets

U.S. PATENT DOCUMENTS

| | | |
|---|---|---|
| 5,167,145 | 12/1992 | Butler et al. |
| 5,174,963 | 12/1992 | Fuller et al. |
| 5,192,502 | 3/1993 | Attridge et al. |
| 5,211,914 | 5/1993 | Vogel et al. ............................ 422/56 |
| 5,232,668 | 8/1993 | Grant et al. |
| 5,236,940 | 8/1993 | Audiau et al. |
| 5,246,858 | 9/1993 | Arbuckle et al. |
| 5,252,293 | 10/1993 | Drabl et al. |
| 5,277,870 | 1/1994 | Fuller et al. |
| 5,279,294 | 1/1994 | Anderson et al. |
| 5,304,468 | 4/1994 | Phillips et al. ........................... 435/14 |
| 5,306,623 | 4/1994 | Kiser et al. ............................. 435/14 |

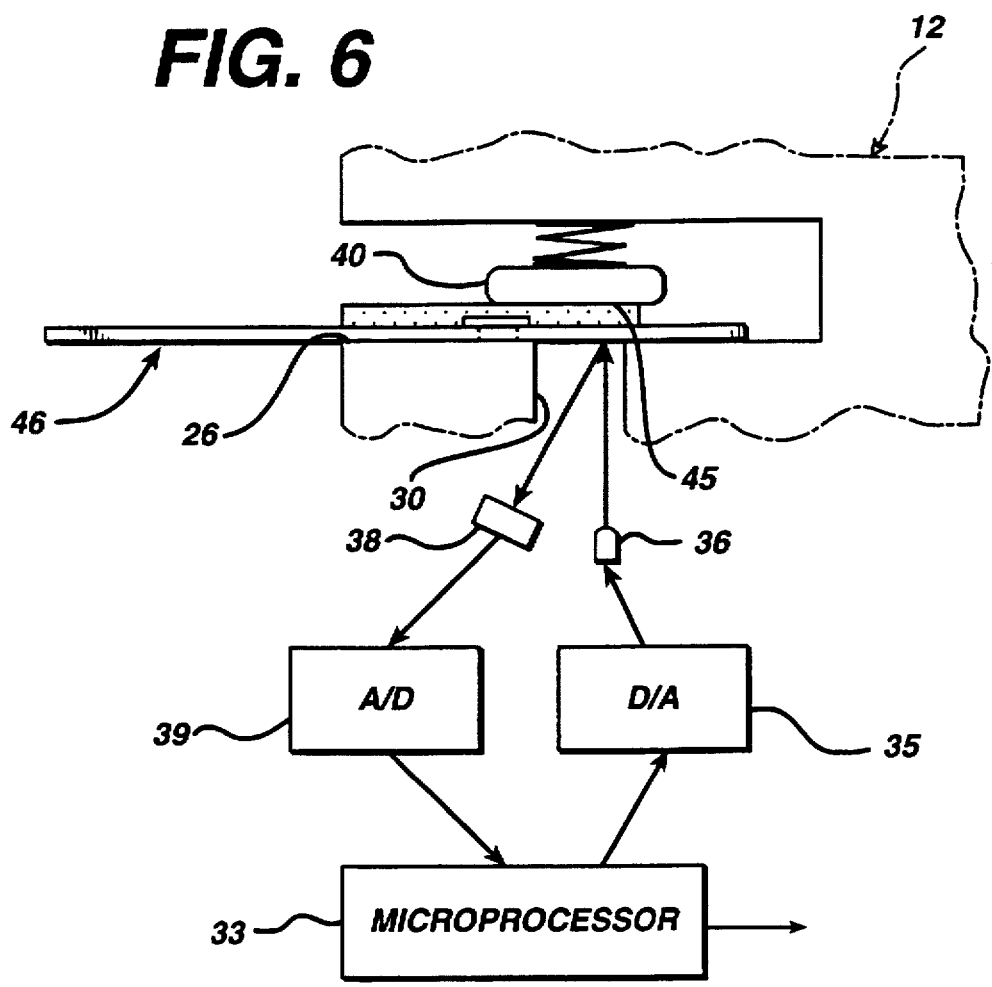

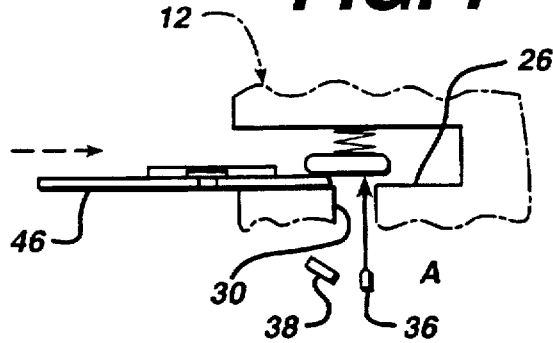
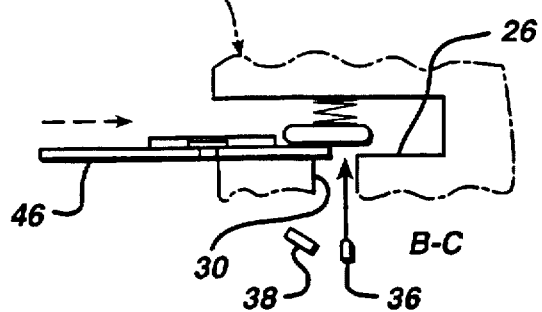
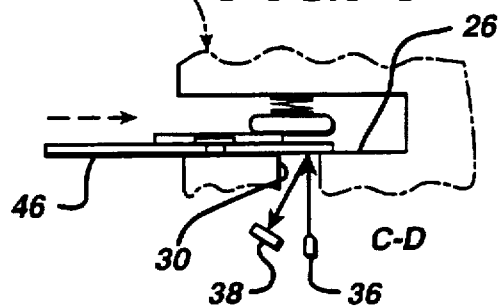
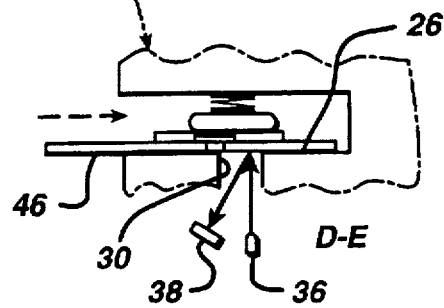
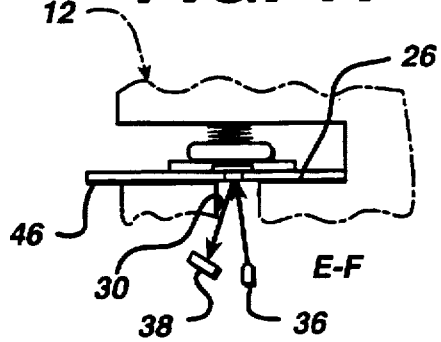
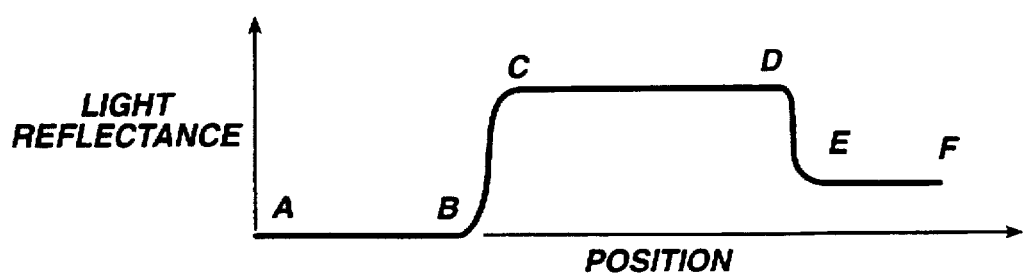

METHOD AND APPARATUS FOR ANALYTE DETECTION HAVING ON-STRIP STANDARD

This is a continuation of application Ser. No. 08/302,160, filed Sep. 8, 1994 now abandoned.

FIELD OF THE INVENTION

The present invention relates to a test device and method for the optical determination of analytes in aqueous fluids, particularly whole blood. In one preferred embodiment it concerns a test device and method for optically measuring the concentration of glucose in whole blood.

BACKGROUND OF THE INVENTION

The quantification of chemical and biochemical components in colored aqueous fluids, in particular colored biological fluids such as whole blood and urine and biological fluid derivatives such as blood serum and blood plasma, is of ever-increasing importance. Important applications exist in medical diagnosis and treatment and in the quantification of exposure to therapeutic drugs, intoxicants, hazardous chemicals and the like. In some instances, the amounts of materials being determined are either so minuscule—in the range of a microgram or less per deciliter—or so difficult to precisely determine that the apparatus employed is complicated and useful only to skilled laboratory personnel. In this case the results are generally not available for some hours or days after sampling. In other instances, there is often an emphasis on the ability of lay operators to perform the test routinely, quickly and reproducibly outside a laboratory setting with rapid or immediate information display.

One common medical test is the measurement of blood glucose levels by diabetics. Current teaching counsels diabetic patients to measure their blood glucose level from two to seven times a day depending on the nature and severity of their individual cases. Based on the observed pattern in the measured glucose levels, the patient and physician together make adjustments in diet, exercise and insulin intake to better manage the disease. Clearly, this information should be available to the patient immediately.

Currently a method widely used in the United States employs a test article of the type described in U.S. Pat. No. 3,298,789 issued Jan. 17, 1967 to Mast. In this method a sample of fresh, whole blood (typically 20–40 µl) is placed on an ethylcellulose-coated reagent pad containing an enzyme system having glucose oxidase and peroxidase activity. The enzyme system reacts with glucose and releases hydrogen peroxide. The pad also contains an indicator which reacts with the hydrogen peroxide in the presence of peroxidase to give a color proportional in intensity to the sample's glucose level.

Another popular blood glucose test method employs similar chemistry but uses, in place of the ethylcellulose-coated pad, a water-resistant film through which the enzymes and indicator are dispersed. This type of system is disclosed in U.S. Pat. No. 3,630,957 issued Dec. 28, 1971 to Rey et al.

In both cases the sample is allowed to remain in contact with the reagent pad for a specified time (typically one minute). Then, in the first case, the blood sample is washed off with a stream of water while in the second case, it is wiped off the film. The reagent pad or film is then blotted dry and evaluated. The evaluation of the analyte concentration is made either by comparing color generated with a color chart or by placing the pad or film in a diffuse reflectance instrument to read a color intensity value.

While the above methods have been used in glucose monitoring for years, they do have certain limitations. The sample size required is rather large for a finger stick test and is difficult to achieve for some people whose capillary blood does not express readily.

In addition, these methods share a limitation with other simple lay-operator colorimetric determinations in that their result is based on an absolute color reading which is in turn related to the absolute extent of reaction between the sample and the test reagents. The fact that the sample must be washed, blotted or wiped off the reagent pad after the timed reaction interval requires that the user be ready at the end of the timed interval and wipe or apply a wash stream at the required time. The fact that the reaction is stopped by removing the sample leads to some uncertainty in the result, especially in the hands of the home user. Overwashing, overblotting, or overwiping can give low results and underwashing can give high results.

Another problem that often exists in simple lay-operator determinations is the necessity for initiating a timing sequence when blood is applied to a reagent pad. A user will typically have pricked his or her finger to obtain a blood sample and will then be required to simultaneously apply the blood from the finger to a reagent pad while starting a timer with his or her other hand, thereby requiring the use of both hands simultaneously. This is particularly difficult since it is often necessary to insure that the timer is started only when blood is applied to the reagent pad. All of the prior art methods require additional manipulations or additional circuitry to achieve this result. Accordingly, simplification of this aspect of reflectance reading instruments is desirable.

Great improvements have been achieved upon the introduction of the systems described in U.S. Pat. Nos. 5,179,005, 5,059,394, 5,049,487, and 4,935,346 wherein an apparatus is provided for accepting a test strip having a test pad, one surface of which comprises a reaction zone adapted to be optically readable by said apparatus. The test strip is inserted into the apparatus, the apparatus is started and then whole blood is applied onto the test pad. At least a portion of such blood is allowed to permeate to the reaction zone whereby any analyte present therein will react with color-producing reagents in the test pad to alter the light reflectance characteristics of the reaction zone. The reflectance of the reaction zone is then a measure of the presence and/or quantity of analyte present in the blood sample. As described in the aforementioned patents, this system does not require a large sample of blood nor does it require the user to undertake timed manipulations with respect to the beginning or end of the reaction. Instead, because the strip is first inserted into the apparatus prior to the application of the sample, a standard reflectance reading of the reaction zone in the dry state may be obtained. The beginning of the reaction can be detected by the first "breakthrough" of the liquid sample onto the reaction zone by monitoring the reflectance and comparing the reading to the standard reflectance of the dry reaction zone. A reflectance reading taken after a predetermined time after the reaction has begun, and compared to the standard reflectance, i.e., the dry reaction zone reading, will be indicative of the quantity of analyte present in the sample.

While the above described system does indeed solve the problems of the prior art and relieves the user of the burden of measurement and timing, it does require that the user apply a sample of blood onto the strip while the strip is in the apparatus. For the most part this represents no problem to the vast majority of users. However, certain users suffer from handicaps such as poor vision or impaired motor coordination so that the accurate application of blood from such users' pricked fingers to the strip, in place on the apparatus, represents a hardship. Further, for institutional users, for example, there is the possibility that some quantity of blood remains on the device from a prior user since the systems necessitate applying one's pricked finger to the device. In such instances there is the need to disinfect the device between users.

Accordingly, for the above reasons, in the case of at least some users, it would be preferable to first apply the blood sample to the strip prior to inserting the strip into the apparatus. Unfortunately, by doing so the apparatus no longer has the capability of reading reflectance of the dry, unreacted, reaction zone, i.e., at no time is the dry reaction zone presented to the apparatus. This reading was necessary in the prior devices to provide a calibration standard for determining the reflectance change as a result of the reaction and hence the presence and/or quantity of the analyte in the sample.

Certain prior systems have been devised to provide the apparatus with such a calibrated standard so as to allow a strip, with a sample already applied, to be introduced into the apparatus. In each such instance, however, the prior systems have complicated the user's tasks in obtaining a reading and have required the user to employ multiple steps in operating such prior systems.

For example, the system described in U.S. Pat. No. 4,125,372 to Kawai discloses a test strip that includes two regions with essentially identical optical characteristics wherein one region undergoes a color change in the presence of the analyte and the other region does not. In this way, color variations of the changing region may be determined against the calibrated reading of the unchanging region after the strip is inserted. The calibration process, however, requires that the user insert the strip in steps. Firstly, the strip is inserted into a first position wherein the user manually adjusts a calibration knob to obtain a standard reading based on the non-color changing region. Then the user inserts the strip into a second position to obtain a reading of the color changing region which is then compared to the first reading to obtain a value for the quantity of analyte present. Obviously these multiple steps are undesirable and particularly so with respect to a handicapped user. In U.S. Pat. No. 5,037,614 to Makita again a multi-step process is disclosed wherein the user first inserts a clean test strip into an apparatus, then obtains a calibrated standard value, then removes the strip, then applies the sample and then reinserts the strip, each time activating the appropriate mode of operation of the apparatus.

In the devices described in U.S. Pat. Nos. 5,277,870 and 5,174,963 to Fuller, a replaceable calibrated disk element, specific to a lot of test strips, is separately employed to provide a calibrated standard. There is, however, no means for compensation for the deterioration of such external standard disk with time. In addition, there is the inconvenience of the multiple steps of inserting the disks and then the strip.

Accordingly, there is a need for a strip, apparatus, and methodology for allowing the user to apply a sample to the strip before inserting it into the reading apparatus while also providing a calibrated standard for the determination of analyte presence and/or quantity; all without the need for excessive manipulation, multiple steps or the danger of the deterioration or the misplacing of some separate calibration standard.

SUMMARY OF THE INVENTION

In accordance with the teachings of this invention, a test strip for determining the presence and/or quantity of an analyte in a liquid sample is provided which can be employed by first applying the sample to the strip and then inserting the strip into an optical reading apparatus. This is accomplished without requiring the user to perform additional manipulations to provide the apparatus with a calibrated standard to compare against the sample-containing strip.

Specifically, the test strip comprises a leading edge, a trailing edge, and a portion for having the liquid applied thereto, this portion having an optically visible surface (i.e., at least with respect to the optics of the apparatus to be employed with the strip) defining a reaction zone. The reaction zone is such that its reflectance varies as a function of the quantity of analyte present in the applied liquid. Preferably, such is accomplished by the analyte, if present, reacting with reactants to produce a color change of the reaction zone. The test strip further comprises an optically visible standard zone having, along its length, a substantially constant reflectance. Preferably, the standard zone has a substantially constant high reflectance, relative to the reflectance of the reaction zone. The standard zone is positioned on the strip so as to lead the reaction zone as the strip is inserted into the apparatus. The standard zone of choice extends from the reaction zone toward the leading edge for a distance of at least 0.3 inches.

Accordingly, the apparatus may be provided with optical means for sequentially determining the reflectance value of the standard zone as the strip is being inserted into its fully inserted position in the apparatus and the reflectance value of the reaction zone after the strip has been inserted. Additionally, the apparatus is provided with means for calculating the presence and/or quantity of the analyte in question as a function of the standard zone reflectance and the reaction zone reflectance.

Owing to the configuration of the strip of this invention and specifically, the provision of a standard zone leading the reaction zone, the aforementioned apparatus need be provided with only one set of optics, e.g., one light emitting diode and one light detector for reading the reflectance at a single position along the path of the strip. Preferably for reasons described herein, reflectance at two specific wave lengths is desirable and hence two light emitting diodes are provided, albeit both focused on the same position along the path of the strip.

In operation, the user turns on the apparatus, applies the sample to a fresh strip and then inserts the strip fully into the apparatus and reads the results. Without intervention of the user, the strip, configured in accordance with the teachings of this invention, allows the apparatus to read the reflectance of light incident upon the standard zone as it passes the optics of the apparatus as the strip is inserted. The reading is employed to then calibrate the apparatus to account for variations owing to changes in the apparatus from the factory condition and to lot-to-lot variations in the strip. The fully inserted strip thereafter presents the reaction zone to the optics of the apparatus and the reflectance of this surface may be read. Means are provided for the apparatus to calculate and report the analyte presence or concentration as a function of these readings.

BRIEF DESCRIPTION OF THE DRAWINGS

The present invention can be more readily understood by reference to the following detailed description when read in conjunction with the attached drawings wherein:

FIG. 6 is a schematic, longitudinal, cross-sectional view of the strip of FIG. 4 inserted into the apparatus, and the means for reading the strip;

FIGS. 7–11 are schematic, longitudinal, cross-sectional views of the strip of FIG. 6 in various sequential positions as it is inserted into the apparatus;

FIG. 12 illustrates a plot of the light reflectance measured by the apparatus as a function of time as the strip is inserted into the apparatus.

DETAILED DESCRIPTION OF THE INVENTION

Figure 1:
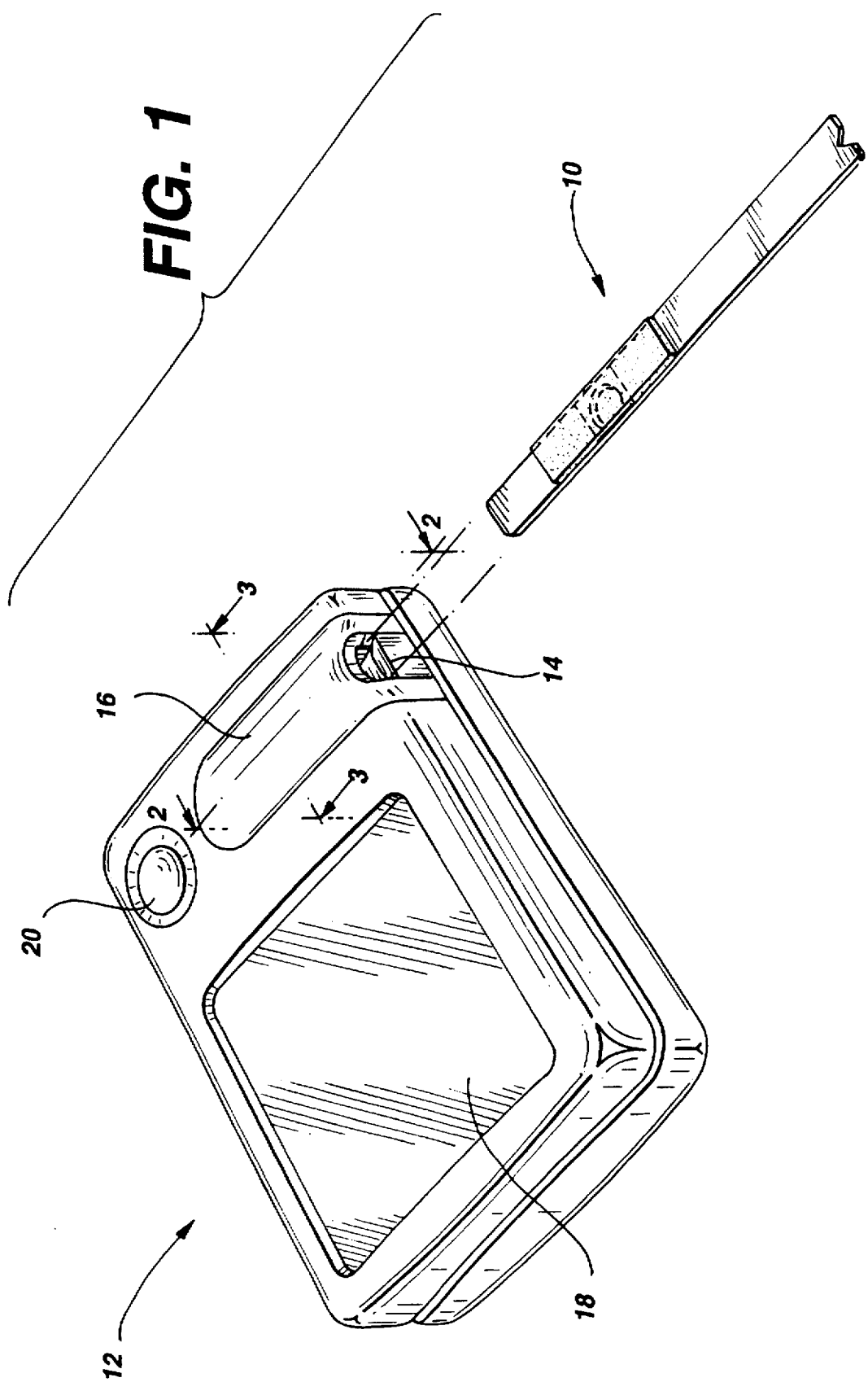
FIG. 1 is an exploded, perspective view of a strip and apparatus embodying the teachings of this invention.

Turning now to the drawings, FIG. 1 illustrates an exploded, perspective view, a strip 10 for applying a sample thereon and for inserting such sample laden strip 10 into an optical reading apparatus 12. This embodiment of the strip 10 and apparatus 12 will generally be described hereinafter in terms of detection and quantification of glucose but it will be understood by those skilled in the art that the teachings herein are not limited to glucose determinations, but instead may be applied to other analyte determinations. Further, for the purposes of simplification and clarity, the strip 10, the apparatus 12 and their respective component parts shall all be described as being in the orientation shown in the drawings and terms such as "the bottom" and "the top" shall be employed consistent with such orientation. It will be appreciated, however, that this method of description is merely convenient and that in no way is the invention restricted to such orientation and, in fact, the strip and strip holder may be rotated through any angle relative to the apparatus and the teachings herein still apply.

Figure 2:
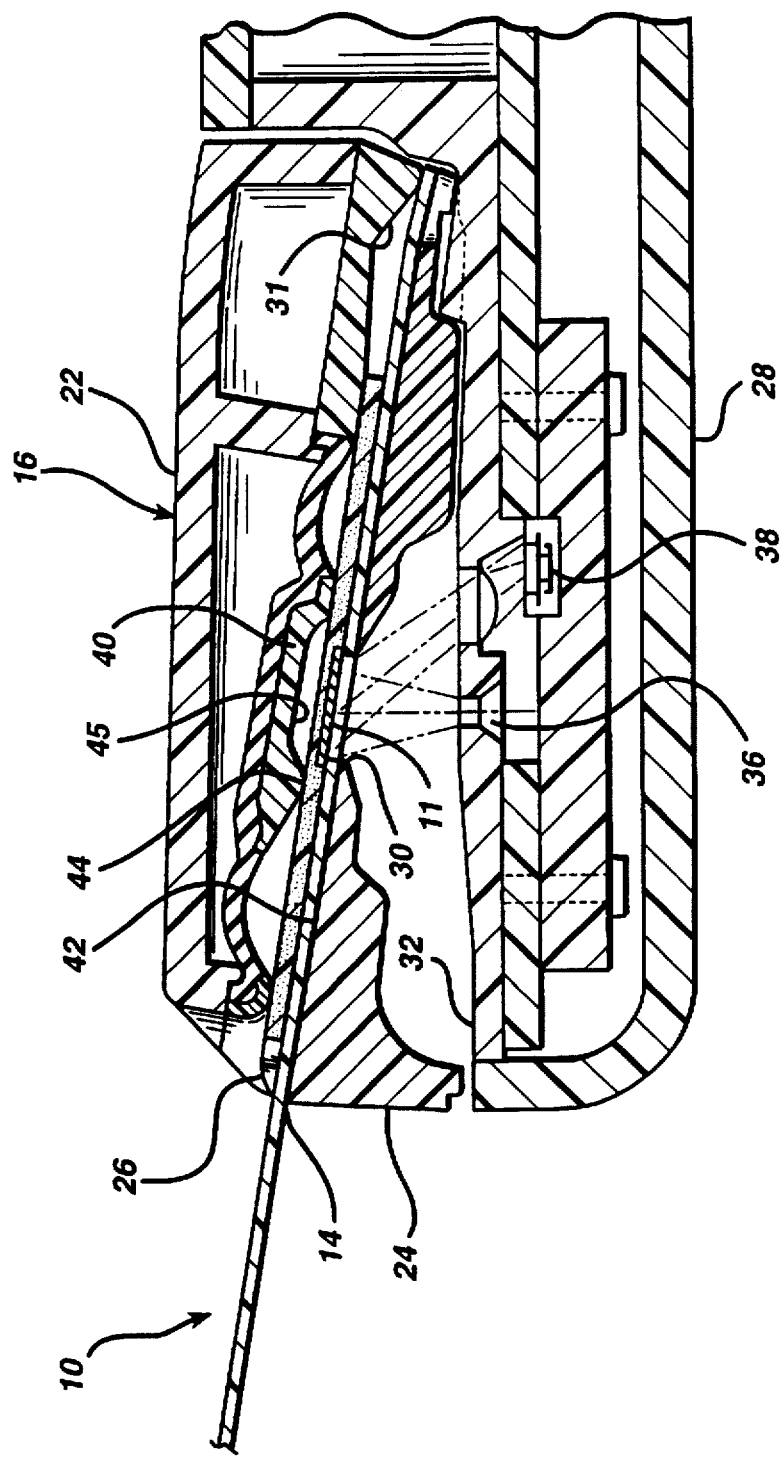
FIG. 2 is a partial, longitudinal, cross-sectional view taken along line 2—2 of FIG. 1 and illustrating the strip fully inserted into the apparatus.
Figure 3:
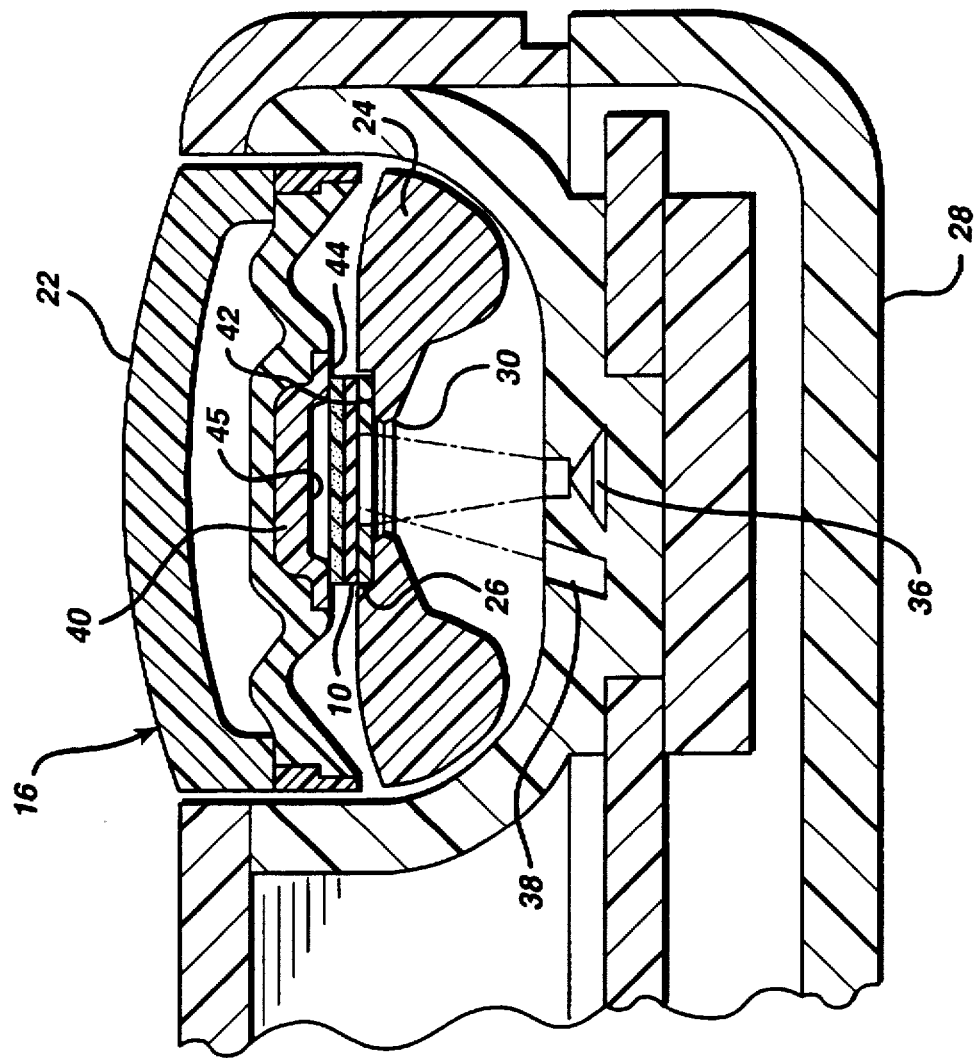
FIG. 3 is a partial, transverse, cross-sectional view, taken along line 3—3 of FIG. 1 and illustrating the strip fully inserted into the apparatus.

As can be seen in FIG. 1, the strip 10 is adapted to be inserted longitudinally, into an opening 14 of a strip holder 16 carried on apparatus 12. Strip holder 16, shown in more detail in FIGS. 2 and 3, is preferably removable from apparatus 12 for cleaning. The apparatus 12 is provided on its visible surface with a screen 18 on which messages, instructions, error warnings, and most importantly, results may be displayed by means such as liquid crystal displays as are well known in the art. Such information may be conveyed by letters, words, numbers or icons. Additionally, apparatus 12 is provided with a power switch for activating the apparatus, preferably with batteries and such power switch is shown as push button 20 on the drawings.

Referring now to FIGS. 2 and 3, illustrated therein in longitudinal and transverse cross-sectional views respectively, is the removable strip holder 16 with a strip 10 fully inserted therein, together with fragmentary views of the adjacent parts of the apparatus 12. The strip holder 16 is comprised of an upper guide 22 and a lower guide 24 which together form a channel or strip passageway 26 into which the strip is inserted via opening 14. The extent of full insertion of the strip is determined by strip impeding wall 31. It should be noted that the passageway 26 is canted at an angle with respect to the plane of the bottom 28 of the apparatus 12, so as to facilitate the insertion of strip 10 into the apparatus when the apparatus is sitting on a flat surface.

The lower guide 24 is provided with an aperture 30 through which the bottom surface 11 of the strip 10 can be "seen" by the optics located below lower guide 24. As will be understood hereinafter, the aperture 30 is positioned along the lower guide 24 so as to "see" the bottom surface of a reaction zone of strip 10 when the strip 10 is fully inserted into passageway 26.

The optics for the apparatus are located in optic block 32 affixed to apparatus 12. Optic block 32 contains a light emitting diode (LED) 36 capable of directing light through aperture 30, upon a surface such as the lower surface of the strip. The light emitting diode is preferably one which emits light of essentially a uniform wavelength in rapid bursts, hereinafter referred to as "chops", for a period of time, each time it is activated. For the purposes of glucose determination it has been found preferable to employ two such LED'S, each emitting light at a different wavelength and preferably at 660 and 940 nanometers (LED 660 and LED 940, respectively). The optic block 32 also comprises a photodetector 38, a device capable of intercepting light reflected from the surface upon which the LED's focus and converting such light into a measurable voltage.

Incorporated into the upper guide 22 is bias means 40 which is adapted to be biased toward the upper surface 42 of the lower guide in the area of the aperture 30 so as to ensure that the portion of the strip 10 lying over the aperture 30 is flat and presents an optically consistent surface to the optics. As illustrated in the drawings, bias means 40 comprises an elastomeric membrane having, on its surface opposing the aperture, a ring-like projecting gasket 44 which is adapted to bear against the strip when in place and hold the strip flat to the aperture. Centered within the ring-like projection is a colored target, preferably gray, hereinafter referred to as the "gray target" 45. As will be described in greater detail herein, the gray target 45 presents to the optics a surface for assuring the correct calibration of the apparatus before the strip is inserted.

Figure 13:
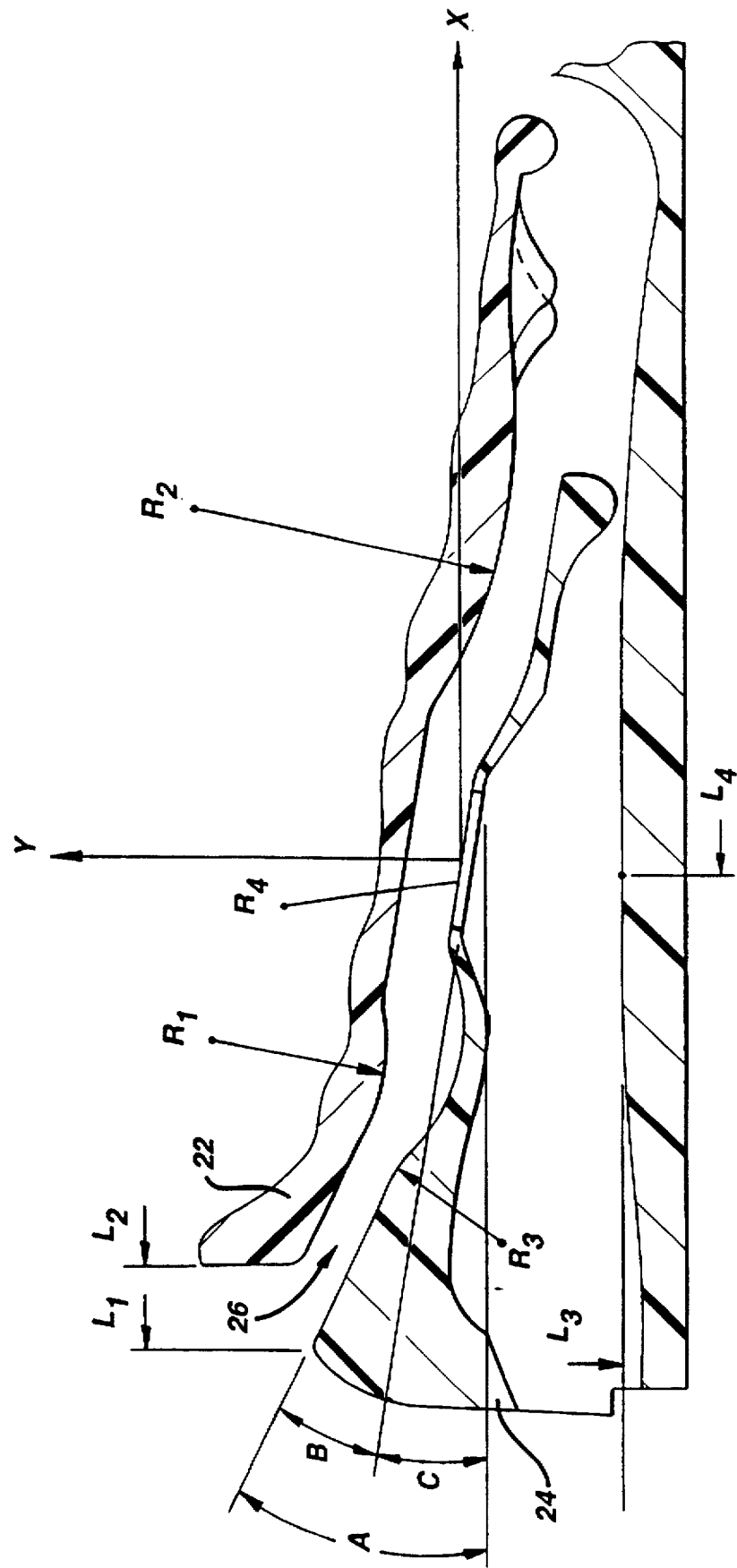
FIG. 13 illustrates a detail of a strip passageway shown in longitudinal cross-section.

The bias means 40 may take forms other than that of an elastomeric membrane. For example, a leaf spring can be used as such bias means. In commonly assigned copending U.S. patent application Ser. No. 08/302,282, filed Sep. 8, 1994 filed on this same day and bearing (incorporated herein by reference), such alternative bias means are described and include a particularly useful means in which the passageway 26 is designed in a serpentine configuration which in combination with a strip having spring properties serves to function as a bias means. Such a passageway is illustrated in FIG. 13 wherein upper guide 22 and lower guide 24 are shown.

Table 1, below, recites preferred dimensions for the angles, distances and radii; all being based on the X.Y coordinates shown in FIG. 13.

TABLE 1

DIMENSIONS FOR FIG. 13

| ANGLES (Degrees) | |
|---|---|
| A | 26 |
| B | 17 |
| C | 9 |

| DISTANCES (Inches) | |
|---|---|
| $L_1$ | 0.562 |
| $L_2$ | 0.467 |
| $L_3$ | 0.184 |
| $L_4$ | 0.013 |

| CURVATURE | | |
|---|---|---|
| | RADIUS (Inches) | CENTER (X, Y In) |
| $R_1$ | 0.2 | 0.207, 0.179 |
| $R_2$ | 0.347 | 0.391, 0.300 |
| $R_3$ | 0.100 | 0.417, 0.006 |
| $R_4$ | 2.635 | 0.412, 2.603 |

Figure 4:
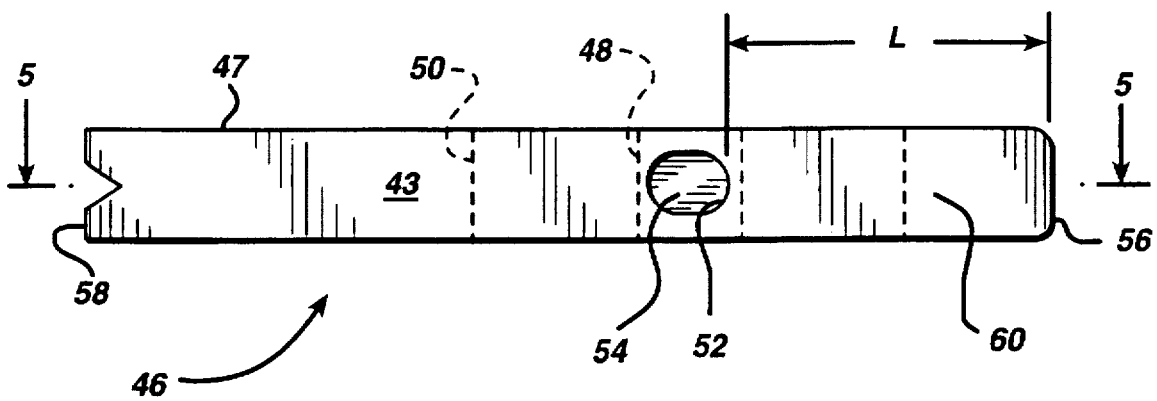
FIG. 4 is a planar view of a major surface of a strip embodying the teachings of this invention.
Figure 5:
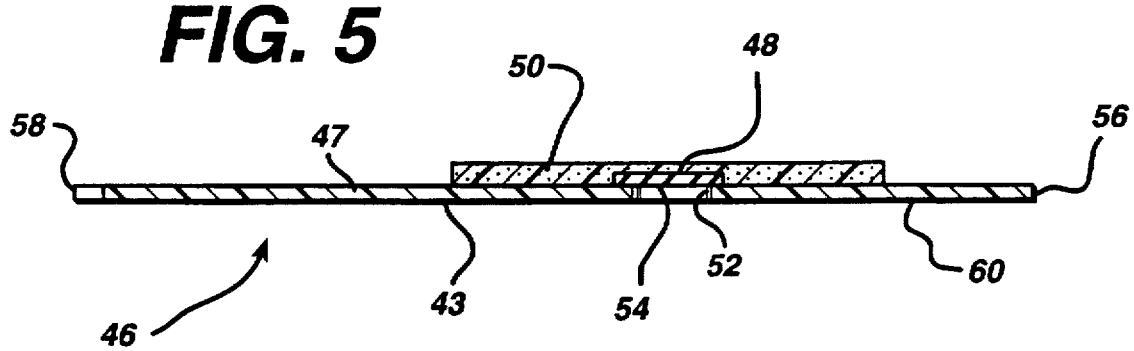
FIG. 5 is a longitudinal cross-sectional view of the strip of FIG. 4, taken along 5—5 of FIG. 4.

Referring now to FIG. 4 illustrated therein is a planar view of the bottom surface 43 of a strip 46 embodying the teachings of this invention. FIG. 5 is a longitudinal, cross-sectional view of strip 46, taken through line 5—5 of FIG. 4.

In the embodiment described herein for detecting glucose in whole blood, the strip 46 comprises an elongate and generally rectangular support 47 onto which is attached a test pad 48 containing reactants and provided with an overlying transport medium 50. In use the sample is to be applied to the top surface of the transport medium 50 overlying the test pad 48. A portion of the sample penetrates through the test pad and any glucose present reacts with the reactants therein to produce a color change which is visible on the bottom surface of the test pad. A support aperture 52 is provided through the support for aligning with aperture 30 in the lower guide of the apparatus when the strip is fully inserted therein, so that a portion of the bottom of the surface of the test pad will be visible to the optics of the apparatus (such portion hereinafter, the reaction zone).

Details of these components of the strip are described in copending U.S. Ser. No. 230,447, filed Apr. 20, 1994 and incorporated herein by reference. Briefly, the transport medium 50 comprises pores which drain the sample therethrough by capillary action. The transport medium may be composed of natural materials such as cotton or paper, as well as such synthetic materials as polyesters, polyamides, polyethylene and the like.

The transport medium has pores having an effective diameter in the range of about 20 microns to about 350 microns, preferably about 50 to about 150 microns, e.g., 100 microns. The transport medium is generally hydrophilic or may be rendered hydrophilic by treatment with surfactants compatible with red blood cells. One such compatible surfactant is MAPHOS™ 66 sold by Mazer Chemical, a division of PPG Industries Inc. Chemicals of Gurnee, Ill. In a preferred embodiment, the transport medium is capable of absorbing blood samples of up to about 20 to about 40 microliters, e.g. 30 microliters.

The transport medium may be, for example, a filter paper or sintered plastic material, such as those porous polyethylene materials commonly available from the Porex Corp. of Fairburn, Ga. The transport medium is generally fabricated to have a thickness of about 0.022 inch, with about 0.25 inch width and about 1.0 inch length. The transport medium is treated with a red blood cell compatible surfactant solution. Since only about 3 to about 5 microliters of blood are required to saturate the testing pad, the transport medium will preferably possess a small void volume in order not to require large volumes of blood. Excess blood applied to the reagent strip is absorbed and held in the portion of the transport medium which extends beyond the test pad.

The test pad and its preparation are also set forth in detail in U.S. Pat. No. 4,935,346 and need not be described in detail herein. Essentially, the test pad is a hydrophilic porous matrix to which reagents may be covalently or non-covalently bound. Examples of a suitable material include polyamides, which are conveniently condensation polymers of monomers of from 4 to 8 carbon atoms, where the monomers are lactams or combinations of diamines and dicarboxylic acids, polysulfones, polyesters, polyethylene, and cellulose based membranes. Other polymeric compositions may also be used. Further, the polymer compositions may be modified to introduce other functional groups so as to provide for charged structures, so that the surfaces may be neutral, positive, or negative, as well as neutral, basic, or acidic. The material of choice is a hydrophilic, anisotropic polysulfone membrane having pores varying in size from large to small through the thickness of the matrix. The preferred matrix is obtained from the Memtec America Corporation of Maryland and has an average pore size of from about 125 to about 140 micrometers e.g., 130 micrometers. The ratio of the average diameter of the large to the small pores is about 100.

The transport medium 50 is attached to the test pad 48 by an adhesive (not shown). Suitable adhesives for this purpose include acrylic, rubber, and ethylene vinyl acetate (EVA) based formulations. Particularly useful adhesives are the hot melt adhesives known in the art. The adhesive may be placed in continuous stripes located only near the perimeter of the test pad, leaving a central portion of the receiving surface of the test pad substantially unobstructed.

Alternatively, when the transport layer is composed of a material that fuses at industrially practical temperatures, the transport layer may be attached directly to the test pad by an application of heat and pressure. The transport layer is heated until it begins to melt and then pressed against the testing pad and cooled. Direct attachment of the transport layer to the testing pad by fusion obviates any need for a distinct adhesive layer.

The transport medium is adapted to accept a whole blood sample and transport a detectable portion of the sample to the receiving surface by capillary action. The transport medium preferably extends past one or more ends of the test pad so as to form a reservoir for holding excess amounts of blood sample which may be present during actual use. It is usually more desirable to retain such excess amounts of the blood sample in the transport medium, rather than allowing the excess to drip upon the user or upon the viewing means in an uncontrolled fashion. Accordingly, it is preferred that the transport medium be capable of holding from about 20 to about 40 microliters of blood, preferably about 30 microliters of blood and of passing from about 3 to about 5 microliters of blood to the test pad.

The test pad is impregnated with a color forming reagent system specific to an analyte. Typical analytes are glucose, cholesterol, urea, and many others which will readily occur to those skilled in the art. Preferably, the color forming reagent system includes an enzyme which selectively catalyzes a primary reaction with the analyte of interest. A product of the primary reaction may be a dye which undergoes a change in color that is detectable at the reaction zone. Alternatively, the product of the primary reaction may be an intermediate which undergoes another reaction, preferably also enzyme catalyzed, and participates in a secondary reaction which, directly or indirectly, causes a final dye to undergo a change in color which is detectable at the reaction zone.

An exemplary color-forming reagent system is the system which is specific to glucose and contains glucose oxidase, a peroxidase, and an oxidizable dye. Glucose oxidase is an enzyme, usually obtained from Aspergillus Niger or Penicillium, that reacts with glucose and oxygen to produce gluconolactone and hydrogen peroxide. The hydrogen peroxide so produced, catalyzed by a peroxidase enzyme, such as horseradish peroxidase, oxidizes a dye. The resulting chromophore (the oxidized dye) exhibits a color that may be observed at the reaction zone. Many suitable oxidizable dyes are known in the art including, for example, those set out in U.S. Pat. No. 5,304,468 incorporated herein by reference. One particularly useful oxidizable dye is the 3-methyl-2-benzothiazolinone hydrazone hydrochloride/8-anilino 1-naphthalenesulfonate dye couple (MBTH/ANS couple) described in copending U.S. patent application Ser. No. 245,940, filed May 19, 1994 (LFS-30). Many other suitable color-forming reagent systems specific to particular analytes are known in the art. A dye couple of choice is a derivative of MBTH, meta|3-methyl 2-benzothiazolinone hydrazone| N-sulfonyl benzenesulfonate monosodium coupled with ANS. This combination is described in detail in U.S. patent application Ser. No. 08/302,575, filed Sep. 8, 1994 and incorporated herein by reference.

The support 47 may be of a material having the properties of being sufficiently rigid to be inserted into the apparatus without undue bending or kinking. Preferably, such support is comprised of materials such as polyolefins (e.g., polyethylene or polypropylene), polystyrene or polyesters. A preferred material for this support is a polyester material sold by the Imperial Chemical Industries Limited of Great Britain under the trademark Melinex 329, in thicknesses of about 0.014 inches.

As viewed in FIG. 4, the bottom surface of the strip (i.e., the surface to be inserted in face-to-face relationship with the aperture 30 of the lower guide of the apparatus and hence the surface "seen" by the optics of the apparatus), can be seen to present a reaction zone 54 comprised of the portion of the test pad 48 visible through the support aperture 52. The reaction zone 54 is longitudinally placed between the leading edge 56 of the strip (leading with respect to insertion into the apparatus) and the opposite edge 58. In accordance with the teachings of this invention, a standard zone 60 is provided on this bottom surface of the strip, at least a portion of which is positioned between the leading edge 56 of the strip and the reaction zone 54. As illustrated in FIG. 4, the standard zone extends longitudinally from the leading edge to the reaction zone i.e., over the dimension L. As will be described in greater detail, the standard zone provides a calibrated standard reflectance value against which the reflectance of the color-developed reaction zone may be measured so as to allow the apparatus to compute and report the presence or quantity of the analyte in question in the sample. The standard zone is placed so as to lead the reaction zone as the strip is inserted into the apparatus whereby the reflectance of the standard zone may be measured as it passes over the optics during the process of the insertion. The standard zone should exhibit reflectance of a given incident light which is substantially constant along its length. Preferably the reflectance of light of 660 nanometers wavelength should not vary within the length of the standard zone by more than from about 70% to about 100% based on the maximum reflectance of such light within the standard zone. It is also preferable that the reflectance within the standard zone contrast with the reflectance of the color-developed reaction zone and more preferably is of higher reflectance. For example, when employing a light source having a wavelength of 660 nanometers, the standard zone is preferably capable of reflecting at least four times as much light as a color-developed reaction zone which has had a whole blood sample applied thereto containing 100 milligrams per deciliter of glucose. Still more preferably, when employing a light source having a wavelength of 660 nanometers, the standard zone is capable of reflecting from about four to about nine times as much light as a color-developed reaction zone which has had a whole blood sample applied thereto containing 100 milligrams per deciliter of glucose. The reflectance of the material of the standard zone and the material of the color-developed reaction zone may be measured with a spectrophotometer available from the Macbeth Company, a division of Kollmorgen, Inc., of Little Britain, Newburgh, N.Y., model number 545.

The requisite reflectance for the standard zone may be obtained by any number of ways as will occur to one skilled in the art. For example, the support may have laminated to it, in the region of the standard zone, a layer having the requisite reflectance. Alternatively, the material comprising the support may have incorporated therein a coloring material imparting the proper reflectance to the region comprising the standard zone. As further alternatives, the coloring material may be printed or painted on the appropriate region. Preferably, as illustrated in FIGS. 4 and 5, the entire support strip is comprised of a material colored to meet the reflectance requirements of the region of the standard zone. In this case there is no clearly visible boundary for the standard zone when viewed by the naked eye. Of course, in such case the optics will only read as the reflectance of the standard zone that portion of the support extending from the leading edge up to the beginning of the reaction zone.

It will be appreciated that since the apparatus must read the value for reflectance of the standard zone as the strip is being inserted into the strip passageway 26, the time available for reading such value will be a function of the velocity at which the strip is inserted and the length of the standard zone, i.e., the dimension L. It has been determined that the highest speed that a user is apt to employ when inserting the strip is less than about 3.5 inches per second and that an accurate reading may be obtained when the standard zone is at least about 0.3 inches and preferably at least about 0.4 inches, e.g., 0.55 inches.

Figure 4A:
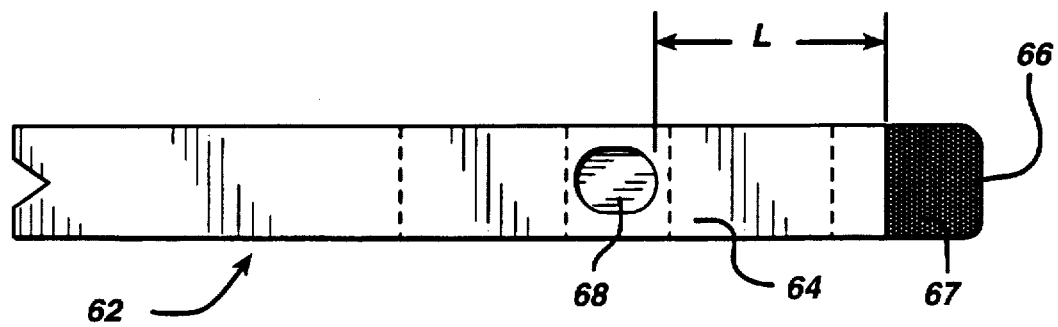
FIG. 4a is a planar view, similar to that of FIG. 4, of an alternative embodiment of the strip of this invention.

FIG. 4A illustrates an alternative strip 62 wherein a standard zone 64 is provided which does not extend to the leading edge 66 but instead extends, for a length of dimension L, from somewhat inward of the leading edge to the reaction zone 68. In this embodiment, the portion 67 from the leading edge 66 to the beginning of standard zone 64 is provided with reflective properties in sharp contrast to the standard zone, e.g., a low reflectance as contrasted with a high reflectance for the standard zone. Accordingly, the apparatus may be programmed to expect first a low reflectance followed by a high reflectance if the strip has been properly inserted with the bottom surface facing the optics. Should the apparatus fail to detect such abrupt change as the strip is being inserted, means may be provided for reporting the error, i.e., the strip has been inserted upside down. It should be noted, of course, that this means of detecting an upside down strip is based on providing a different reflectance pattern on the opposite surface of the strip.

To better understand the strip of this invention and the mode of using the same, reference is made to FIG. 6 which illustrates schematically the functional features of the apparatus as the strip is inserted therein together with FIGS. 7–11 which schematically illustrate the strip in various positions during the insertion process.

As illustrated in FIG. 6, a strip 46 such as that described in connection with FIGS. 4 and 5 is being inserted in the direction of the arrow, into the strip passageway 26 of apparatus 12. A bias means 40 is provided to urge the strip flat against the aperture 30 to ensure consistent optical performance. The bottom surface 45 of the bias means 40 presents the gray target to the optics of the system when no strip is in place. Within the apparatus and focused on the surface presented through aperture 30 is at least one LED 36. For the purposes of glucose determination, two such LED's are employed emitting beams of light at 660 and 940 nm, respectively. A photodetector 38 is positioned to detect light reflected from the surface presented to the aperture 30 and communicate such detected light to an analog/digital convertor (A/D) 39 whereby reflected light is converted from a voltage into a digitized signal which, in turn, is communicated to microprocessor 33. The microprocessor also communicates to the LED's 36 via a digital/analog convertor (D/A) 35 to control the sequence of operations of the LED's in accordance with the programmed operation of the apparatus. The microprocessor also controls the operation of the output, i.e., the instructions, messages, and results reported on the liquid crystal display screen of the apparatus.

FIGS. 7–11 illustrate, schematically, sequenced positions of the strip with respect to the aperture 30 as the strip is inserted into passageway 26. Thus, in FIG. 7 the strip 46 has just been inserted into the passageway and the leading edge has not yet reached the aperture. Accordingly, the surface presented to the optics is solely the gray target at the bottom of the bias means (position A). In FIG. 8, the leading edge and the beginning of the standard zone have partially occluded the aperture and hence the optics see portions of both the gray target and the standard zone (positions B through C). In FIG. 9, the strip has totally occluded the aperture 30 and the optics see only the standard zone (positions C through D). In FIG. 10, the interface between the standard zone and the reaction zone, lies over the aperture 30 and the optics see portions of both zones (position D through E). Finally, referring to FIG. 11, the strip is fully inserted and the optics see only the reaction zone (positions E through F).

The reflectance of the surface presented to the optics is measured by the apparatus at each of these positions. Multiple readings are taken at each position in spaced periods of time. Each such reading comprises a number of bursts of energy imparted to the LED in response to directions from the microprocessor. These bursts, referred to as chops, control the amount of light energy directed to the surface for each reading, i.e., at a constant power level, the greater the number of chops the greater the light energy incident upon the surface being measured. The light energy reflected by the surface during each reading is captured by the photodetector and converted into a voltage. The voltage is allowed to decrease to zero over a period of time and the time it takes to decrease to zero is a measure of the light energy absorbed by the photodetector, i.e., the light reflected from the surface being measured. Such time period is measured in units called counts and hence the number of counts represents the light energy reflected from the surface. FIG. 12 is a plot of the counts or light energy reflected from the surface presented to the aperture as a function of the position of the strip as it is inserted into the apparatus. The position of the strip corresponding to FIGS. 7 through 11 are noted by the corresponding letters A through F. Thus, referring to FIG. 12, when the strip is in the position shown in FIG. 7 (positions A through B) only the gray target is presented and the light reflectance is at a low constant value. When the strip is in position B through C, the gray target is being occluded by the highly reflectant standard zone and hence the light reflection detected increases as occlusion proceeds. When the strip is in position C to D, the standard zone is presented to the optics and the light reflection becomes a constant high value. When the strip is in position D through E an increasing proportion of the aperture is presented with the relatively low reflective surface of the reaction zone and a decreasing portion of the relatively high reflective standard zone and hence the light reflection detected rapidly decreases. Finally, when the strip reaches positions E through F and beyond only the reaction zone is visible to the optics and a relatively low constant light reflectance is detected.

With the above described relationship of the strip position and the output of the optical reading apparatus in mind, the calibration and operation of the system will next be described.

It will be understood that each apparatus and strip combination will qualitatively behave as has been described herein. However, variations between specific apparatus, variations in time in a given apparatus and variations in lot to lot manufacture of strips must all be accounted for before an accurate value for an analyte such as glucose in a sample liquid such as blood can be ascertained. To do this, each apparatus must be factory adjusted prior to release and each lot of strips must be coded for its own reflective characteristics so that when the apparatus is turned on and put to use, an internal calibration is made to account for changes in the apparatus after it has left the factory and for changes from lot to lot for the strips.

Firstly, each apparatus must be adjusted to provide the proper quantity of light energy to be emitted by each LED (for glucose LED 660 and LED 940). As has been described, such light energy is a function of the number of chops and the power supplied to the LED. These parameters are adjusted in the factory so as to produce, in a given apparatus, an arbitrarily chosen light reflectance from a white standard zone, such reflectance value arbitrarily being selected at 4,000 counts (the time for the photodetector to degrade accumulated voltage to 0). The degrees of freedom of the system allow the power to be adjusted so as to achieve the goal of about 4,000 counts while constraining the number of chops to a value which is approximately 55 chops per reading. With each of the 660 nm wavelength and 940 nm wavelength LED's set at its own factory determined value of chops (CHP 660 and CHP 940) and power, a reading for the reflectance of the gray target of the apparatus for each LED is made and stored in the microprocessor as the calibrated gray reading for each LED (RCG 660 and RCG 940).

In operational mode in the hands of the user, when a glucose determination is to be made, the user first powers the apparatus. At this point, the microprocessor directs certain diagnostic checks to be made. For example, the battery voltage is checked to assure that it is sufficient. Further, the operating temperature is checked. It will be understood that since the determination of the analyte, e.g., glucose, is dependent upon a chemical reaction occurring within the test pad of the strip, the rate of such reaction going to completion will be a function of temperature. Accordingly, if the temperature is too low or too high, e.g., less than 10° C. or greater than 40° C., the apparatus will report an error. If the temperature is low but still operable, the apparatus will adjust for such low temperature by extending the reading time of the reaction zone.

Having made these diagnostic tests, the microprocessor will adjust the optics (autoscale) to account for any variations occurring after the apparatus has left the factory. As has been described above, with a strip out of the apparatus, the optics view only the gray target. Accordingly, the microprocessor directs a reading of the gray target employing the LED 940 at 3 chops. If the reflectance reading is less than a predetermined value, it is assumed that the gray target is missing or out of position and an error is reported. If the reflectance value is higher than a predetermined value, it is assumed that a strip has been prematurely inserted into the apparatus and again an error message is reported. As is generally the case, when the reflectance reading is between the two predetermined values, the apparatus begins the adjustment or autoscaling as follows. The apparatus views the gray target, reads a value for its reflectance at each LED wavelength using the factory determined number of chops (calibrated CHP 660 and calibrated CHP 940) and compares these values to the factory stored values for the gray reading. If the reading differs, an adjustment is made in the number of chops for each LED to bring the numbers into closer agreement. Such autoscaling is based on the following calculation:

Autoscaled CHOP 660 =

$$\left[ \frac{(\text{Calibrated } CHP\ 660 + 1) \cdot (RCG660)}{(RDG\ 660)} \right] - 1$$

Autoscaled CHOP 940 =

$$\left[ \frac{(\text{Calibrated } CHP\ 940 + 1) \cdot (RCG940)}{(RDG\ 940)} \right] - 1$$

wherein RDG 660 and RDG 940 are the current gray target readings from LED 660 and LED 940, respectively.

In the event that the adjustment exceeds a predetermined limit, the apparatus will report an error.

The microprocessor then causes the apparatus to advise the user, via the screen, to apply a sample to a strip and then insert the same into the apparatus. At this time, the microprocessor initiates the procedure for detecting the leading edge of the standard zone. This is accomplished by rapid readings of the reflectance of the surface presented to aperture 30 using LED 940 at a low number of chops per reading, e.g., three chops per reading. If a reflectance is read which is greater than a predetermined number of counts, chosen to be an indicia of a highly reflective surface appearing in the aperture, the leading edge of the standard zone is considered detected.

The apparatus is next programmed to read the reflectance of the standard zone. It has been found that calibrating the reflectance of the standard zone to the maximum reading obtained, provided at least three valid readings are obtained as the strip is inserted, will give accurate results. Accordingly, the microprocessor is programmed to cause the readings to begin, at detection of the strip, with LED 660 and then alternate readings between LED 940 and 660 at a reduced number of chops with respect to the autoscaled number of chops. The reduced number of chops allows more readings in the time available as the strip is inserted and produces adequate resolution for the purposes of calibration. In practice, the microprocessor, for each reading at each wavelength, replaces the prior value stored as the reflectance with the next read value if, and only if, such next read value exceeds the stored value. In this way, only the maximum reflectance reading for each wavelength is stored, after the entire standard zone is scanned.

The maximum reflection reading of the standard zone may then be scaled to the autoscaled number of chops at each wavelength as follows:

$$RW\ 660 = \frac{(\text{autoscaled CHOP } 660 + 1) \cdot (RMX\ 660)}{N}$$

$$RW\ 940 = \frac{(\text{autoscaled CHOP } 940 + 1) \cdot (RMX\ 940)}{N}$$

wherein RMX 660 and RMX 940 are the maximum detected readings for the reflectance of the standard zone and RW 660 and RW 940 are the now calibrated values for the standard zone at the respective autoscaled number of chops for each LED. |N IS EQUAL TO THE REDUCED NUMBER OF CHOPS|

For each of the LED 660 readings, the ratio of such reading to the prior maximum value is calculated. If such ratio falls below a predetermined value, e.g., 0.7, it is assumed that the interface of the standard zone and the reaction zone has been reached. Should this occur before three valid readings for maximum reflection in the standard zone had been made, then the microprocessor shall cause the screen to report an error to the user, assuming that the strip has been inserted too fast. Further, should the reaction zone not be detected within a predetermined time, e.g., 15 seconds, it will be assumed that the strip has not been properly inserted and an appropriate message will appear on the screen.

Having determined the calibration value for the standard zone, a further internal calculation is made to ensure that the optics are not dirty or otherwise impaired by employing the reflectance reading taken on the gray area when the apparatus was first started and the now determined calibrated standard reflectance. It is assumed that, provided the optics are clean and operable, the K/S ratio between the gray target and the standard zone are constant over the life of the product, within a predetermined tolerance, e.g., ±15%. K/S is the calculated value employed in the Kubelka-Monk equations derived specifically for reflectance spectrometry from employment of Beer's Law and described in some detail in U.S. Pat. No. 5,179,005, and in greater detail in Journal of Optical Society of America; Vol. 38; No. 5; May, 1948; pp 448–457. In accordance with the Kubelka-Monk equations:

$$K/S = \frac{(1 - R^*)^2}{2R^*}$$

wherein R* is the ratio of the reflectance in question to a standard reflectance. The K/S for the gray target at each wavelength is determined as a function of the initial reading of the gray target and the calibrated standard zone reflectance to determine if these correspond with the K/S ratios calculated from the factory stored reflectance data for these two, within prescribed tolerances. If not, an appropriate error message is reported.

Once this internal check is completed, the apparatus is programmed to examine the reflectance of the reaction zone and determine when the reaction between the putative analyte (glucose in the described embodiment) and the reactants in the test pad has gone to an end point (within a prescribed tolerance). The end point is detected by reading the reaction zone once every second with the LED 660 at the autoscaled chops until completion is detected. The readings are converted into K/S data as described above (hence a function of the calibrated standard zone reading and the reading taken on the reaction zone) until no change, within prescribed limits, is detected in the K/S reading and it can be assumed that the end point has been reached.

In addition to detecting the end point by reading the reaction zone with the LED 660, another reading is made by the LED 940 after a predetermined interval during the end point detection process, e.g., 30 seconds after the process has begun. This is made to assure that a reflectance reading is within prescribed ranges indicative of the fact that a proper amount of sample has been deposited on the test pad. Should these ranges be transgressed, an error will be reported.

Having determined that the end point has been reached and the proper quantity of sample has been applied, calculations are next made to determine the analyte (glucose) content of the sample. The last K/S data taken from a reading of the reaction zone when the end point has been detected, KS660, is employed and is first corrected for the factory determined calibration using a linear correlation, e.g.:

$$KSMCAL = F(KS660) + G$$

wherein F and G are coefficients provided to the microprocessor of the particular apparatus in the factory. The KSM-CAL value is further corrected to provide for idiosyncrasies in an individual manufacturing lot of strips. Each lot has been tested in the factory and given a single code number. The code number references a set of coefficients, e.g., 21 sets stored in the microprocessor of each apparatus and indexed against said code number. For example, a linear correlation is believed adequate to account for lot to lot variations in the strips in the glucose test and hence two coefficients per set are stored against each code number. Upon inserting a strip into the apparatus, the user will be asked to enter the proper code number found on the package of the strips being employed. The microprocessor will then, employing a look-up table, be apprised of the proper coefficients. It will be understood that the strip itself may be provided with an apparatus readable code thereby obviating the need to enter the same. In any event, the apparatus corrected K/S ratio KSMCAL, is further corrected with respect to the strip, as:

$$KSSCAL = (KSMCAL)M + B$$

wherein KSSCAL is now the strip corrected K/S ratio and M and B are the looked-up coefficients. Finally, the analyte (glucose) concentration, preferably in units of mg/dl of sample, is calculated in accordance with a trinomial correlation:

$$G = K_1 + K_2(KSSCAL) + K_3(KSSCAL)^2 + K_4(KSSCAL)^3$$

wherein G is the glucose concentration and $K_1$, $K_2$, $K_3$, and $K_4$ are empirically derived constants.

Alternatively, a look-up table which reflects such correlation may be supplied to the microprocessor.

The invention having now been fully described, it will be apparent to one of ordinary skill in the art that modifications and changes can be made thereto without departing from the spirit or scope of the invention as defined in the following claims.

What is claimed is:

1. An apparatus for determining the presence or quantity of an analyte in a sample applied to a portion of a longitudinally extending test strip; said portion having an optically visible surface defining a reaction zone which reaction zone varies in reflectance as a function of the quantity of analyte present in the applied liquid; said apparatus comprising:

an opening for inserting the leading edge of said strip into said apparatus;

a strip passageway extending from said opening and terminating at a strip impeding means for impeding the strip after it is fully inserted;

an optical aperture through said passageway whereby a portion of the surface of the strip overlying said aperture is visible, said aperture positioned along said passageway so that when said strip is fully inserted said reaction zone of said strip is visible therethrough;

optics, in optical communication with said optical aperture, said optics comprising at least one light source for directing light onto said portion of said strip and at least one reflectance detector for detecting light reflected from said portion of said strip;

a microprocessor for controlling the optics as the strip is being inserted into the passageway and after the strip has reached the strip impeding means;

said microprocessor being programmed to cause said light source and detector to make a plurality of readings of a standard zone provided on the surface of the strip leading the reaction zone and visible through the optical aperture as the strip is being inserted, and use the highest reading to provide a calibrated standard reflectance;

said microprocessor being programmed to cause said light source and said detector to read the reflectance of the reaction zone after the strip has been inserted; and said microprocessor being programmed to determine the quantity of analyte in the sample as a function of said calibrated standard zone reflectance and the reflectance of the reaction zone; and means for reporting such quantity.

2. A method for determining the presence or quantity of an analyte in a liquid applied to a test strip and inserted into an optical reading apparatus, said method comprising:

applying liquid to said test strip wherein said test strip comprises a portion having a surface defining a reaction zone which varies in reflectance as a function of the quantity of analyte present in said applied liquid and further comprises a standard zone of substantially constant reflectance;

inserting said strip into said apparatus with said standard zone leading said reaction zone as said strip is inserted;

taking a plurality of readings of the reflectance of said standard zone as said strip is inserted;

reading the reflectance of said reaction zone after said strip is inserted;

employing the highest of the standard zone reflectance readings and the reaction zone reflectance reading to determining the presence or quantity of the analyte in the liquid as a function of these reflectance readings.

3. The method of claim 2 where at least three readings are taken of the standard zone.

* * * * *